(12) United States Patent
Qiao et al.

(10) Patent No.: US 8,980,628 B2
(45) Date of Patent: Mar. 17, 2015

(54) HAIR FOLLICLE PRECURSOR PRODUCTION BY CO-CULTURING MAMMALIAN DERMAL PAPILLA CELLS AND KERATINOCYTES

(75) Inventors: Jizeng Qiao, Lexington, MA (US); Jeffrey Keeler Teumer, Brookline, MA (US); Erica Jean Philips, Lowell, MA (US)

(73) Assignee: Aderans Research Institute, Inc., Beverly Hills, CA (US)

( * ) Notice: Subject to any disclaimer, the term of this patent is extended or adjusted under 35 U.S.C. 154(b) by 1251 days.

(21) Appl. No.: 12/293,402

(22) PCT Filed: Mar. 15, 2007

(86) PCT No.: PCT/US2007/006790
§ 371 (c)(1),
(2), (4) Date: Dec. 30, 2008

(87) PCT Pub. No.: WO2007/109223
PCT Pub. Date: Sep. 27, 2007

(65) Prior Publication Data
US 2009/0198336 A1    Aug. 6, 2009

(30) Foreign Application Priority Data

Mar. 17, 2006  (GB) ............................. GB0605450.6

(51) Int. Cl.
| | | |
|---|---|---|
| C12N 5/02 | (2006.01) | |
| A61L 27/38 | (2006.01) | |
| C12N 5/077 | (2010.01) | |
| C12N 5/071 | (2010.01) | |
| C12N 5/0775 | (2010.01) | |

(52) U.S. Cl.
CPC .......... *A61L 27/3886* (2013.01); *C12N 5/0656* (2013.01); *C12N 2502/092* (2013.01); *C12N 2501/415* (2013.01); *C12N 2502/1323* (2013.01); *C12N 5/0628* (2013.01); *C12N 5/0666* (2013.01); *A61L 27/3813* (2013.01); *A61L 2430/18* (2013.01); C12N 5/0627 (2013.01); *C12N 2502/02* (2013.01); *C12N 2502/091* (2013.01); *C12N 2502/094* (2013.01)
USPC ............ 435/373; 435/377; 435/384; 435/395

(58) Field of Classification Search
CPC ......... A61K 35/36; A61Q 7/00; A61Q 5/002; C12N 2502/1323; C12N 2502/092; C12N 2501/415; C12N 5/0628; C12N 5/0656; C12N 5/0666; C12N 5/0627; C12N 2502/094
See application file for complete search history.

(56) References Cited

U.S. PATENT DOCUMENTS

| | | |
|---|---|---|
| 5,851,831 A | 12/1998 | Inamatsu et al. |
| 5,980,888 A | 11/1999 | Dimoudis et al. |
| 7,160,726 B2 * | 1/2007 | Mansbridge .................. 435/391 |
| 7,163,679 B1 * | 1/2007 | Kishimoto et al. ......... 424/93.21 |
| 2002/0172705 A1 | 11/2002 | Murphy et al. |
| 2003/0161815 A1 | 8/2003 | Wolowacz et al. |
| 2004/0057937 A1 | 3/2004 | Jahoda et al. |
| 2004/0170611 A1 | 9/2004 | Morgan et al. |
| 2005/0089512 A1 | 4/2005 | Schlotmann et al. |
| 2005/0233450 A1 | 10/2005 | Goetinck et al. |

FOREIGN PATENT DOCUMENTS

| | | |
|---|---|---|
| EP | 0236014 | 9/1987 |
| EP | 1437042 | 7/2004 |
| WO | WO 98/47471 | 10/1998 |
| WO | 9901034 | 1/1999 |
| WO | 0174164 | 10/2001 |
| WO | 02060396 | 8/2002 |
| WO | WO 03/051419 | 6/2003 |
| WO | 03068248 | 8/2003 |
| WO | WO 2004/044188 | 5/2004 |
| WO | 2005018731 | 3/2005 |
| WO | WO 2005/071063 | 8/2005 |
| WO | WO 2005/084223 | 9/2005 |
| WO | WO 2006/113629 | 10/2006 |

OTHER PUBLICATIONS

Itami et al., Role of androgen in mesenchymal epithelial interactions in human hair follicle, J Investig Dermatol Symp Proc. 10(3):209-11, 2005.*

Matsuzaki et al., Role of hair papilla cells on induction and regeneration processes of hair follicles, Wound Repair Regen. 6(6):524-30, 1998.*

Kamp et al., Regulation of PDGF and PDGF receptor in cultured dermal papilla cells and follicular keratinocytes of the human hair follicle, Exp Dermatol. 12(5):662-72, 2003.*

Havlickova et al., "Towards Optimization of an Organotypic Assay System That Imitates Human Hair Follicle-Like Epithelial-Mesenchymal Interactions," *British Journal of Dermatology*, 151:753-765 (2004).

Ihara et al.,"Formation of Hair Follicles from a Single-Cell Suspension of Embryonic Rat Skin by a Two-Step Procedure In Vitro," *Cell Tissue Res.* 266:65-73, 1991.

(Continued)

*Primary Examiner* — Deborah Crouch
(74) *Attorney, Agent, or Firm* — Pabst Patent Group LLP

(57) ABSTRACT

This invention relates to methods of producing hair folliclesin vitro, compositions for producing hair follicles in vitro, in vitro produced hair follicles, methods of providing an in vitro produced hair shaft at an interfollicular or intrafollicular site, methods of treating hair loss by providing an in vitro produced hair shaft at an interfollicular or intrafollicular site and assays for studying the effect of test agents on hair biology. The invention also provides the similar methods and products which are, or use, immature follicles ("defined herein as proto-hairs"). The invention provides a method for in vitro production of a hair follicle or a proto-hair comprising co-culturing dermal papilla cells with keratinocytes, and optionally with melanocytes.

17 Claims, 9 Drawing Sheets

(56) References Cited

OTHER PUBLICATIONS

Inui et al., "Androgen-Inducible TGF-β1 from Balding Dermal Papilla Cells Inhibits Epithelial Cell Growth: A Clue to Understand Paradoxical Effects of Androgen on Human Hair Growth," *FASEB J.* 16:1967-1969, 2002.
Kishimoto et al., "Selective Activation of the Versican Promoter by Epithelial-Mesenchymal Interaction during Hair Follicle Development," *Proc. Nat'l. Acad. Sci. USA* 96:7336-7341, 1999.
Na et al., "Isolation and Characterization of Outer Root Sheath Melanocytes of Human Hair Follicles," *British Journal of Dermatology*, 155:902-909 (2006).
Nakao et al., "Establishment of a Coculture System Using Immortalized Human Dermal Papilla Cells from Androgenetic Alopecia and Human Keratinocytes," *J. Dermatol. Sci.* 34:124, 2004 (Abstract).
Pan et al., "Role of Testosterone in the Growth of Keratinocytes through Bald Frontal Dermal Papilla Cells," *Endocrine* 11:321-327, 1999.
Reynolds et al., "Hair Follicle Reconstruction In Vitro," *J. Dermatol. Sci.* 7:S84-S97, 1994.
Roh et al., "Dermal Papilla-Induced Hair Differentiation of Adult Epithelial Stem Cells from Human Skin," *Physiol. Genomics*, 19:207-217 (2004).
Satoshi et al., "Pathomechanism of Androgenetic Alopecia and New Treatment," *Jap. J. Geriatrics* 41:598-600, 2004 (English Abstract Only).
Troy and Turksen, "ES Cell Differentiation into the Hair Follicle Lineage In Vitro," *Methods Mol. Biol.* 185:255-260, 2002.
Search Report for GB0605450.6, Jul. 7, 2006.
Search Report for GB0605450.6, Dec. 11, 2006.
International Search Report and Written Opinion of (PCT/US2007/006790) mailed Aug. 30, 2007.
Inamatsu, et al., "Establishment of rat dermal papilla cell lines that sustain the potency to induce hair follicles from afollicular skin", J. Invest. Dermatol., 111 (5):767-775 (1998).
Itami, et al., "Role of androgen in mesenchymal epithelia interactions in human hair follicle", J. Investig Dermatol Symp Proc., 10(3):209-11 (2005).
Jahoda, et al., "Dermal-Epidermal Interactions, Adult Follicle-Derived Cell Populations and Hair Growth", Dermatologic Clinics, 14(4):573-583 (1996).
Jahoda, et al., "Induction of hair growth by implantation of cultured dermal papilla cells", Nature, 311(5986):560-562 (1984).
Kishimoto, et al., "Wnt signaling maintains the hair-inducing activity of the dermal papilla", Genes Dev., 14(10)1181-1185 (2000).
Matsuzaki, et al., "Role of hair papilla cells on induction and regeneration processes of hair follicles", Wound Repair Regen., 6(6):524-30 (1998).
Misago, et al., "Proliferation and differentiation of organoid hair follicle cells co-cultured with fat cells in collagen gel matrix culture," British Journal of Dermatology, 139: 40-48 (1998).

\* cited by examiner

Figure 1
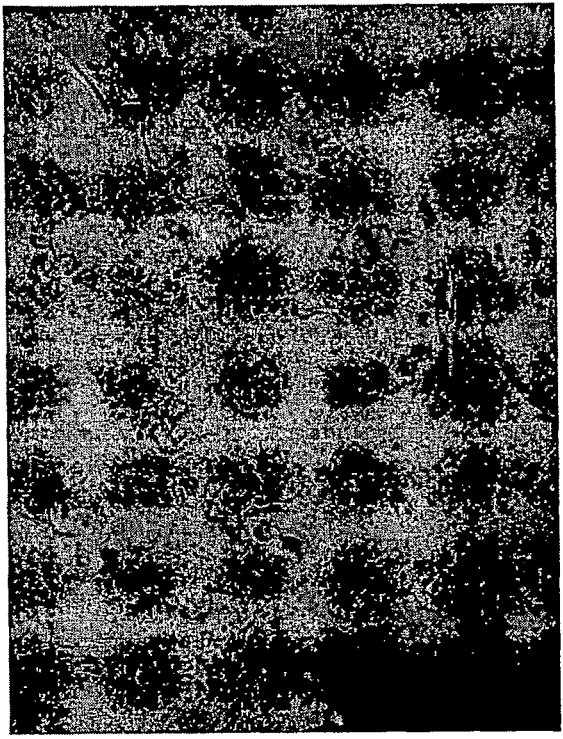
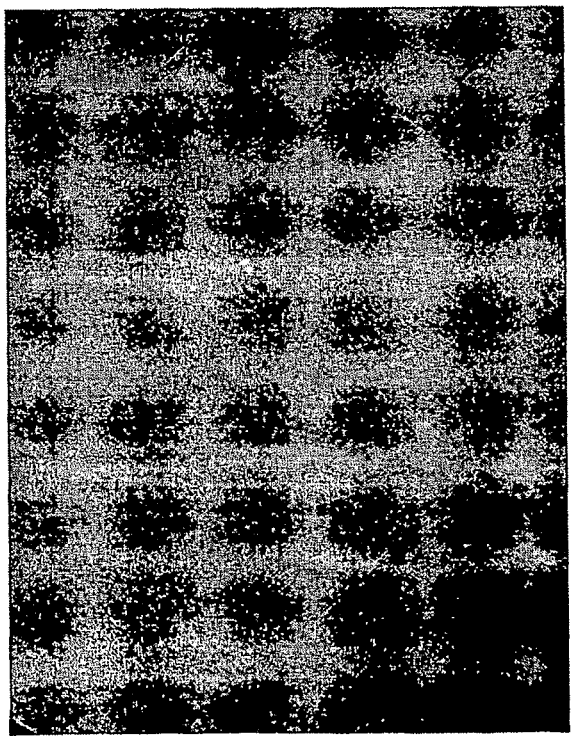

Figure 9
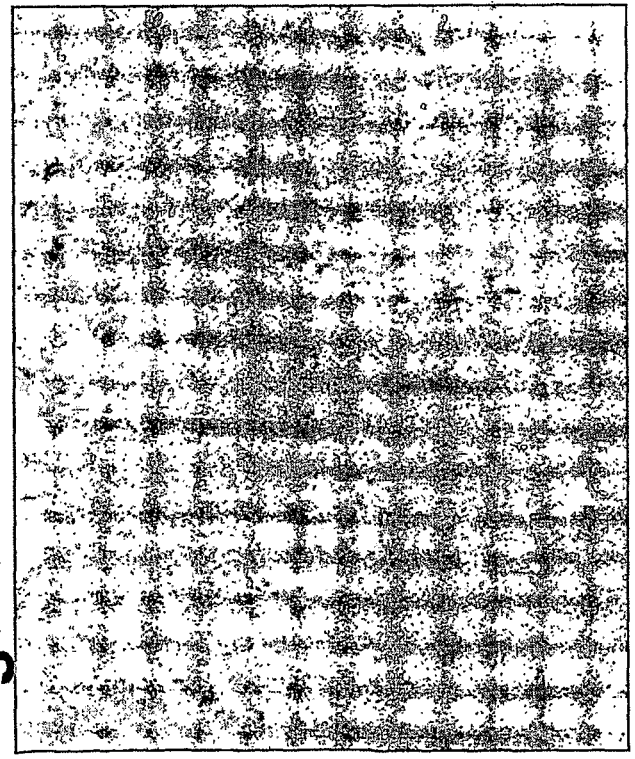
A
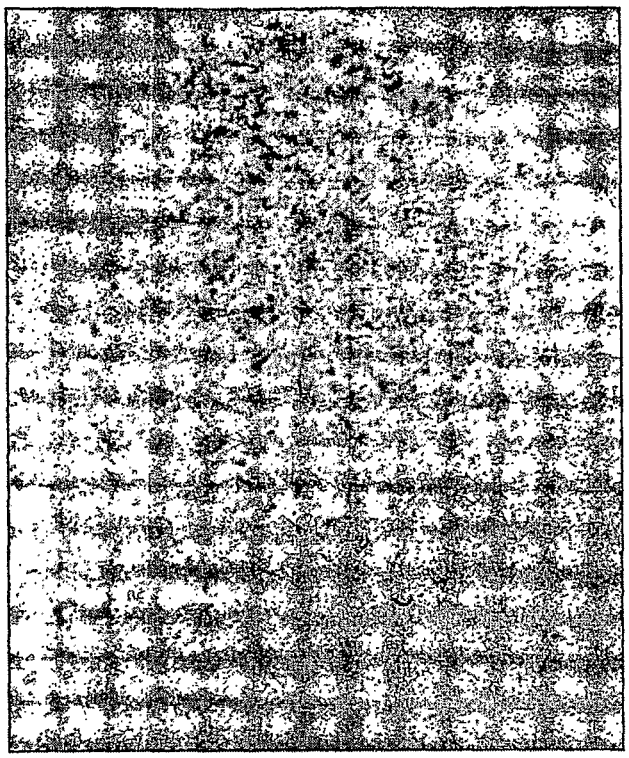
B

HAIR FOLLICLE PRECURSOR PRODUCTION BY CO-CULTURING MAMMALIAN DERMAL PAPILLA CELLS AND KERATINOCYTES

CROSS-REFERENCE TO RELATED APPLICATIONS

This application claims priority under 35 U.S.C. §371 from International Application No. PCT/US2007/006790, filed on Mar. 15, 2007, and claims priority from Great Britain Application No. 0605450.6, filed on Mar. 17, 2006, both of which are incorporated by reference herein.

BACKGROUND OF THE INVENTION

This invention relates to methods of producing hair follicles in vitro, compositions for producing hair follicles in vitro, in vitro produced hair follicles, methods of providing an in vitro produced hair shaft at an interfollicular or intrafollicular site, methods of treating hair loss by providing an in vitro produced hair shaft at an interfollicular or intrafollicular site and assays for studying the effect of test agents on hair biology. The invention also provides the similar methods and products which are, or use, immature follicles ("defined herein as proto-hairs").

SUMMARY OF THE INVENTION

Mammalian skin is composed of two layers, an outer layer called the epidermis and an inner layer called the dermis. The epidermis is several cell layers thick, is comprised of mainly keratinocyte cells, and has an external layer of dead cells that are constantly shed from the surface and replaced from below by a basal layer of cells, the stratum germinativum. The dermis comprises a network of collagenous extracellular material, elastic fibres, blood vessels, nerves and hair follicles with associated sebaceous glands.

During embryogenesis, the establishment of a dermal papilla is vital to the development of hair follicles and associated modified structures like sebaceous glands. The dermal papilla is a group of specialised dermal fibroblast cells, derived from the embryonic mesoderm. These dermal papilla cells begin to aggregate in the dermis just below the epidermis. Above the dermal papilla an epidermal plug, or peg, of cells develops and proliferates growing into the dermis towards the dermal papilla. The mesoderm-derived dermal papilla and the ectoderm-derived epidermal plug communicate via molecular signals with the result of further proliferation of epidermal matrix cells and differentiation into the various sheath and hair fibre structures. Thus the development of a hair follicle requires a continuum through induction, initiation, elongation and differentiation stages.

A mature hair follicle comprises a bulb containing the dermal papilla cells, a hair shaft extending from the bulb, and a dermal sheath, which provides an external covering of tissue around the bulb and along the length of the follicle. The hair follicle extends down through the dermis, a hypodermis (a loose layer of connective tissue below the dermis), and a fat or adipose layer. In adults, molecular signals between the dermal papilla and the epidermal component of a follicle cause the hair to enter an active (anagen) growth phase from an inactive (telogen) phase.

As defined herein, a proto-hair is a precursor of a mature hair follicle. We have for the first time produced such proto-hairs in vitro. A proto-hair may be considered as a part-formed follicle. It can be identified and isolated at a stage of development between the dermal papilla cell stage and the fully formed follicle stage. A proto-hair has a structure which develops from the dermal papilla cell but is no longer a dermal papilla cell as such. The structure of the proto-hair is also not that of a follicle, but it can be seen to have elements of follicle-like structure. A proto-hair is capable of further development. It can develop into a mature hair follicle in a suitable in vitro culture. It can also develop into a mature hair follicle if implanted into a recipient: this means that an in vitro produced proto-hair can subsequently produce a mature hair follicle in vivo.

An in vitro produced mature hair follicle can be implanted into a recipient in order to provide a hair shaft at the implantation site (capable of anagen phase growth in vivo).

Similarly, a proto-hair has a "nascent" or "immature" proto-hair shaft. An in vitro produced proto-hair can be implanted into a recipient where it can develop in vivo into a hair follicle in order to provide a hair shaft at the implantation site (capable of anagen phase growth in vivo).

Hair loss affects millions of people, including over 40% of men over the age of 30 and a significant number of women. Baldness (known medically as alopecia) is defined as the loss of hair from an area of the body. Numerous factors cause hair loss such as destruction by autoimmune reaction or scarring, disease, infection and sensitivity to androgen. In alopecia caused by androgen sensitivity, known as androgenetic alopecia, the androgen dihydrotestosterone causes certain follicles to undergo a progressive miniaturization. The miniature follicle produces a tiny hair shaft that is cosmetically insignificant.

Several methods for treating hair loss are available. Two drug treatments are available, topical Minoxidil™ (Pharmacia) and orally-delivered Propecia™ (Merck). However, these treatments have achieved limited success in restoring natural hair growth and are only effective whilst the drugs are being taken.

An effective surgical treatment is hair follicle transplantation, a procedure in which hair follicles are transplanted from a non-balding region of the scalp to a region of hair loss. This has a number of disadvantages:
- hair transplant surgery is expensive ~10,000 per procedure;
- multiple procedures are often required to give desired effect;
- a complete pattern of hair with high density of follicles cannot readily be obtained using hair follicle transplantation.
- it is limited by donor tissue availability;
- it requires extensive donor tissue removal (2000-5000 follicles);
- if the donor site is large it may result in scarring
- there can be pain, bleeding and swelling during and immediately after implantation; and
- it is currently unregulated.

An alternative to hair follicle transplantation is follicular cell implantation but at present no clinical application of follicular cell implantation is available.

It has now surprisingly been found that hair follicles can be produced in vitro by co-culturing dermal papilla cells with keratinocytes, with the optional addition of melanocytes.

The present invention provides an in vitro method for production of a hair follicle comprising co-culturing a dermal papilla cell with a keratinocyte, and optionally with a melanocyte.

This invention addresses one of the problems of current hair transplantation techniques that there is a limit to the available donor hair. The total number of human scalp hairs is fixed after birth. Similarly the donor hair source for an Alopecia patient is restricted. As hair transplantation does not create any new hair, it simply transfer hairs from one location to another, there is a need for a method of producing further hairs.

It is not necessary for the hair follicle to be fully formed in order for it to develop into a mature hair when transplanted. Surprisingly, we have found that a partially formed follicle structure (proto-hair) generated in vitro will also develop into a mature hair when transplanted.

This invention dramatically decreases the quantity of donor hair tissue required. It has the potential to provide an infinite number of hair follicles or proto-hairs from the cells originally isolated from a few hair follicles, since the cells can be infinitively expanded in vitro.

Source of Cells for Co-Culture

The dermal papilla cells, keratinocytes and melanocytes may be of adult origin.

The dermal papilla cells, keratinocytes and melanocytes may be of embryonic origin.

The dermal papilla cells, keratinocytes and melanocytes may be of primary origin. 'Primary origin' is used herein to mean as cells obtained directly from donor tissue prior to co-culture.

The dermal papilla cells, keratinocytes and melanocytes may be obtained from separate dermal papilla, keratinocyte and melanocyte cultures, respectively.

The dermal papilla cells, keratinocytes and melanocytes may be obtained from any source of stem cells or progenitor cells. For example, embryonic stem cells, bone marrow stem cells, umbilical cord stem cells, any committed hair progenitor cells or semi-committed hair progenitor cells.

The dermal papilla cells, keratinocytes and melanocytes may be of human or xenogenic origin. Preferably the cells are of human origin.

The dermal papilla cells, keratinocytes and melanocytes may be of autologous or allogeneic origin.

The dermal papilla cells keratinocytes and melanocytes may originate from tissue of the head, body or foreskin of a tissue donor.

The keratinocytes may be skin basal keratinocytes, hair keratinocytes, hair bulge keratinocytes, hair matrix keratinocytes, or any mixture of the above.

The melanocytes may be originated from skin, or from hair follicles.

Cells can be derived from the sources in a variety of methods, such as microdissection, enzymatic treatment, or any other method.

Methods of Combining Cells

The dermal papilla cells, keratinocytes with or without melanocytes may be brought together for co-culture in any configuration in which the cells are in close proximity in a manner that promotes hair follicle formation.

For example, cells can be combined in a matrix that may consist of biological materials such as collagen or extracellular matrix.

Alternatively, the dermal papilla cells, keratinocytes with or without melanocyteos may be brought together and cultured in the form of a cell aggregate to develop proto-hair in vitro.

The cell aggregate may be formed in any manner. For examples:
1. The cell aggregate may be prepared in a microcentrifuge tube by centrifugation of a mixture of cells.
2. The cell aggregate may be prepared in a multi-well plate.
3. The cell aggregate may be prepared in using a Methylcellulose solution in a multi-well plate.
4. The cell aggregate may be prepared using a 'hanging droplet' method in which the aggregate forms in a droplet of cells suspended in a culture dish.
5. The cell aggregate may be prepared by any method that brings cells together and creates an environment for cell-cell contact.

The size of aggregate may be varied from few hundreds to few hundred thousands of cells.

The ratio of cell populations in an aggregate (if two or three cell types are involved) may be varied.

Alternatively, the cells can be combined in a culture dish, or a culture dish coated with a matrix, or a transwell membrane, or a transwell membrane coated with a matrix.

Alternatively, the dermal papilla cells can be combine in a configuration with a sheet of keratinocytes.

Media for Co-Culture of Cells

The dermal papilla cells and keratinocytes with or without melanocytes may be co-cultured in a medium that supports hair growth. The medium may be supplemented with substances that further support hair growth and development. For example growth factor(s), such as FGF, TGF-alpha, PDGF, any molecule(s), such as Wnt, GSK-3 inhibitors, Sonic hedgehog or Sonic hedgehog agonists, Noggin or BMP inhibitors, antibodies, iRNA, any chemical compound(s), such as Minoxidil, any cell-conditioned-medium, such as keratinocyte-conditioned medium, may be added into the medium to promote proto-hair development.

A mature hair follicle or a proto-hair may be isolated from the co-culture once it has been produced. A hair shaft may also be isolated from the co-culture in conjunction with any associated cells or tissue.

There is also provided according to the invention an in vitro composition comprising co-cultured dermal papilla cells and keratinocytes, optionally with melanocytes.

There is also provided according to the invention an in vitro composition comprising a dermal papilla cell and a keratinocyte, optionally with a melanocyte, wherein the dermal papilla cell and/or the keratinocyte and (where present) the melanocyte has been isolated from dermal tissue.

There is also provided an in vitro composition comprising a dermal papilla cell and a keratinocyte, optionally with a melanocyte, wherein the dermal papilla cell and/or the keratinocyte and (where present) the melanocyte have been obtained from separate dermal papilla cell, keratinocyte, and melanocyte cultures, respectively.

There is also provided according to the invention an in vitro composition comprising a dermal papilla cell and a keratinocyte, optionally with a melanocyte, wherein the dermal papilla cell and/or the keratinocyte and, (if present) the melanocyte, are part of a cell aggregate.

Preferably the in vitro composition of the invention further comprises a hair follicle or a proto-hair.

An in vitro composition of the invention may further comprise a matrix.

The cells of an in vitro composition of the invention may be in a suspension.

A composition of the invention may further comprise a culture medium.

The invention provides for use of any of the compositions to produce a hair follicle or proto-hair in vitro.

Also according to the invention there is provided an in vitro produced hair follicle or proto-hair.

The invention provides a method of providing a hair follicle or proto-hair at an interfollicular or intrafollicular site, which comprises implanting or delivering an in vitro produced hair follicle or proto-hair at the site.

The present invention provides a method of treating hair loss, which comprises implanting or delivering an in vitro produced hair follicle or proto-hair at an interfollicular or intrafollicular site.

Embodiments of the invention are described in the example below with reference to the accompanying drawings in which:

FIGS. 1A and 1B show proto-hairs forming in a mouse dermal tissue matrix in vitro. FIG. 1A=Day 1, FIG. 1B=Day 2.

FIGS. 2A and 2B show that mature hair follicles will form from proto-hairs isolated and then transplanted from the cultures shown in FIGS. 1A and 1B. FIG. 2A=Isolated proto-hairs ready for transplantation. FIG. 2B=Mature hair formed after implantation of proto-hair.

FIGS. 3A and 3B show proto-hairs developed in vitro from cultured aggregates.

Figure 5:
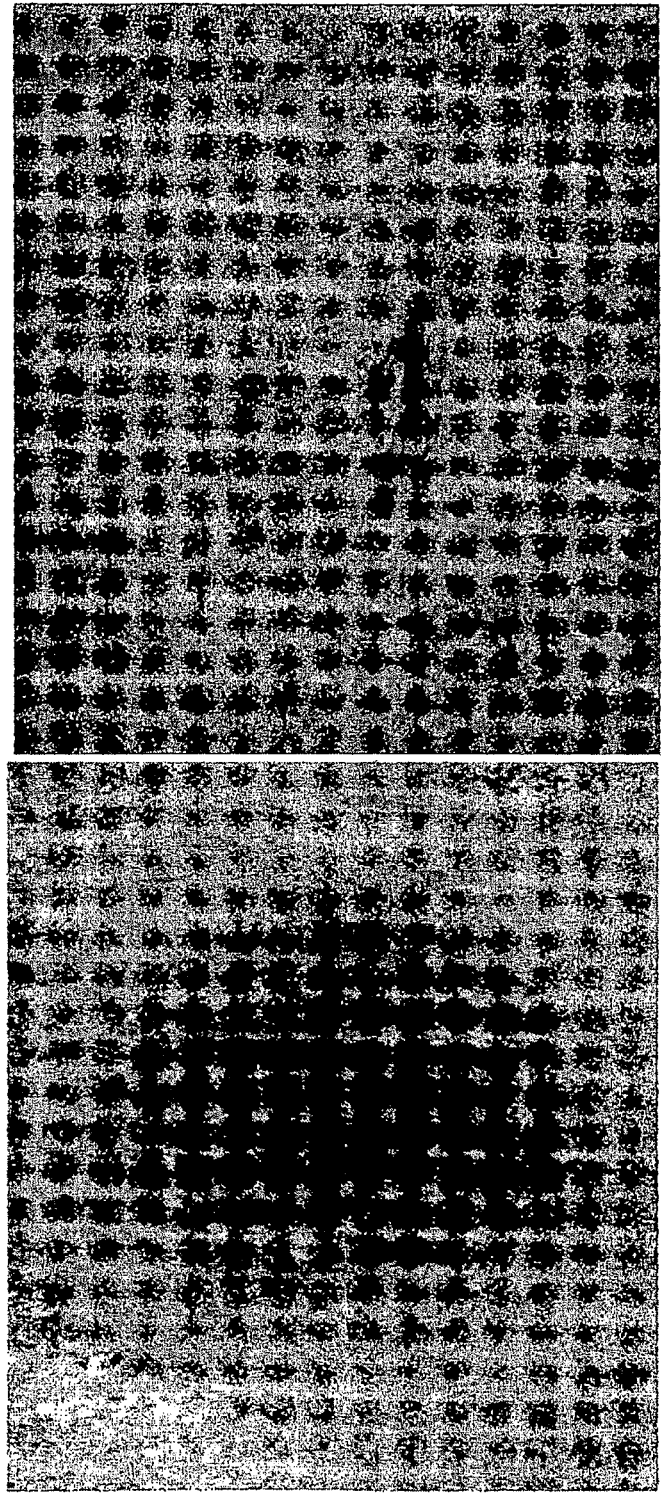

FIGS. 5A and 5B show hair structures forming from dermal papilla cells combined with keratinocytes on a transwell membrane. FIG. 5A=from culture. FIG. 5B=from Histology.

Figure 6:
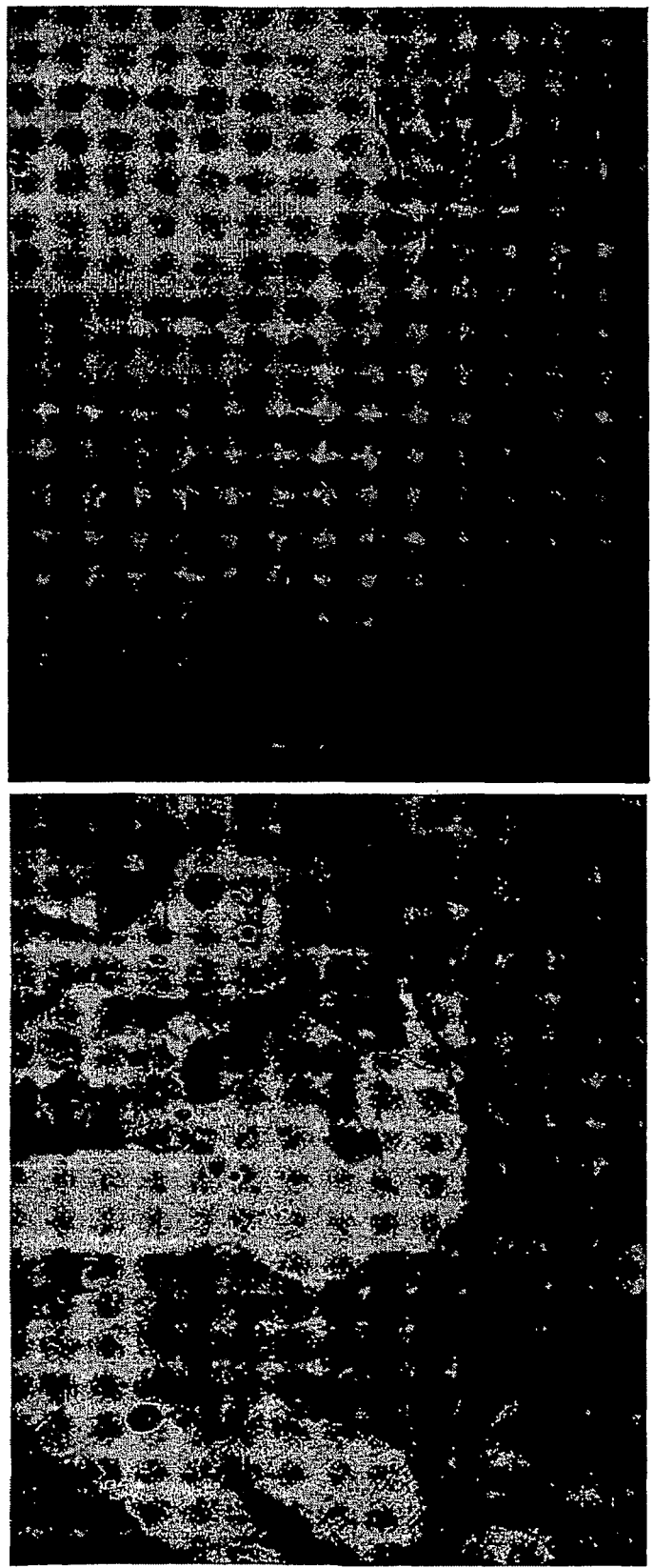

FIGS. 6A and 6B show hair development from cultured dermal papilla cells combined with a sheet of epidermal keratinocytes. FIG. 6A=from culture. FIG. 6B=from Histology.

Figure 7:
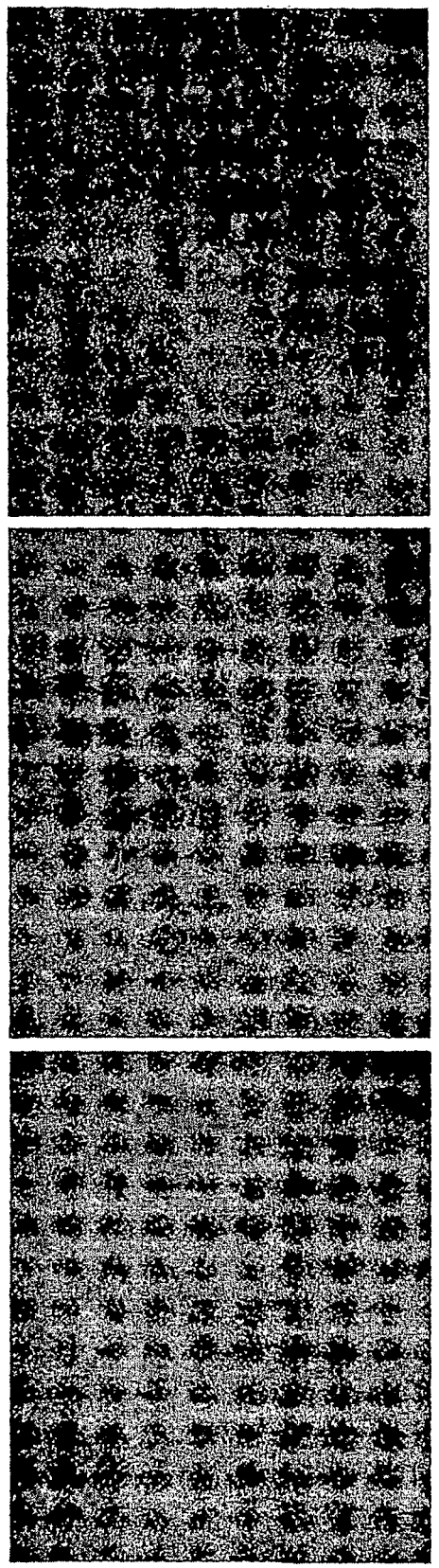

FIGS. 7A, 7B, and 7C show hair development in vitro is inhibited by addition of an antibody to demonstrate the use of the co-culture system as an assay for the effect of an antibody on hair development. FIG. 7A=High Dose Antibody. FIG. 7B=Medium Dose Antibody. FIG. 7C=Very Low Dose Antibody.

Figure 8:
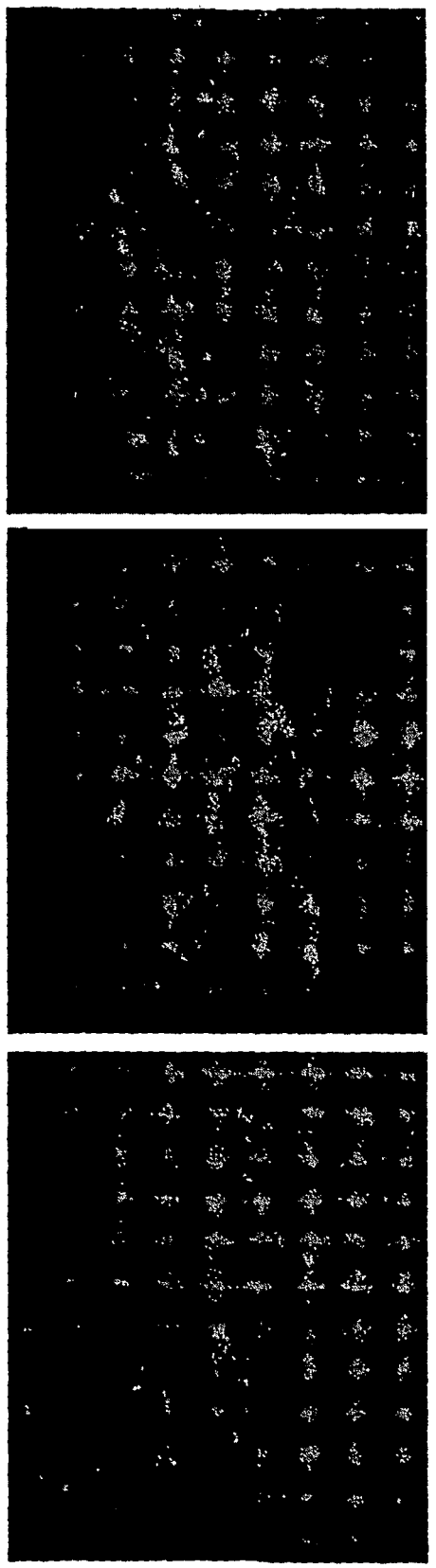

FIGS. 8A, 8B, and 8C show hair development is promoted by addition of a growth factor to demonstrate the use of the co-culture system as an assay for the effect of a growth factor on hair development. FIG. 8A=No Growth Factor. FIG. 8B=Low dose Growth Factor. FIG. 8C=High dose Growth Factor.

FIGS. 9A and 9B show hair development is promoted by addition of a reagent to demonstrate the use of the co-culture system as an assay for the effect of a reagent on hair development. FIG. 9A=No reagent added. FIG. 9B=Reagent added.

EXAMPLES

In-vitro production of hair suitable for transplantation:
Preparation of Dermal Papilla Cells
1. Human hair follicles are dissected out from a small biopsy tissue
2. Dermal papilla are isolated from hair follicle
3. Dermal papilla are cultured in ICX-Chang medium for 10 days at 37 C, 5% CO2.
4. Switch the culture medium to DPGM and continue the culture for another 4 days.
5. Passage cells with Trypsin-EDTA
6. Either continue the culturing the passaged cells in DPGM or freeze down the cells in Liquid Nitrogen in a freezing medium (10% DMSO in DMEM10) for future use.

Preparation of Hair Keratinocytes
1. Hair follicles are collected after dermal papilla have been removed
2. Incubate hair follicles in Dispase overnight at 40 C
3. Hair shaft with outer root sheet are pulled out from hair follicle
4. Collect the hair shaft with outer root sheet and treat with Trypsin-EDTA at 37 C for 15 min or until outer root sheet cells are dissolved into the enzyme solution
5. Add equal volume of serum containing medium to neutralize enzyme activity
6. Filter tissue/cell solution through a 100 um and a 40 um cell drainer sequentially
7. Pellet cells down and re-suspend cells in DMEM10
8. Culture harvested hair keratinocyte cells on feeder cells
9. Medium is periodically changed until it becomes confluent
10. Remove feeder cells with the treatment of EDTA
11. Passage keratinocyte cells in Trypsin-EDTA
12. Either continue the culture of passaged cells on feeder cells or freeze down cells in Liquid Nitrogen in a freezing medium (10% DMSO in DMEM10) for future use.

Preparation of Hair Melanocytes
1. Human hair follicles are dissected from a piece of scalp biopsy tissue
2. Hair follicle ends are cut
3. Matrix tissues above dermal papilla are quizzed out of the hair ends
4. Collect all matrix tissues
5. Incubate matrix tissues with enzyme(s) to yield a single cell suspension
6. Wash cells with serum-free medium
7. Primary cell culture is carried out in proper vessels with/without coating or with/without feeder cells in special melanocyte culture medium at 37° C. and 5% $CO_2$
8. Medium is periodically changed until culture is confluent
9. Passage cells
10. Either continue to culture or freeze cells in 10% DMSO-DMEM10

In vitro production of hair follicles and proto-hairs
1. Aliquot a total amount of cultured dermal papilla cells
2. Aliquot a total amount of cultured hair keratinocytes
3. Aliquot a total amount of cultured melanocytes (if required)
4. Mix the cell populations
5. Pellet down the mixed cell populations
6. Transfer the whole cell pellet onto a trans-well membrane or other matrix
7. Culture in a suitable medium to allow hairs to develop
8. The proper culture medium can be Chang, Epilife, Melanocyte-specific medium or mixture of above. Any growth factor(s), such as FGF, TGF-alpha, PDGF, any molecule(s), such as Wnt, GSK-3 inhibitors, shh or agonist, Noggin or BMP inhibitors, antibodies, iRNA, any chemical compound(s), such as Manoxdil, any cell-conditioned-medium, such as keratinocyte-conditioned medium, wnt-3a conditioned medium, may be added into the medium to promote proto-hair development.

Alternatively,
1. Cell aggregates can be made with either pure dermal papilla cells or a mixture of papillacell populations by several methods:
2. Cells can be dispended into Eppendorf tubes, pelleted and then cultured at 37° C. and 5% $CO_2$ for the formation of aggregates.
3. Cells can be alternatively dispended into a special non-adhesive 96 well plate and cultured at 37° C. and 5% $CO_2$ for the formation of aggregates (special non-adhesive 96 well plate method).
4. Cells can be alternatively re-suspended in a Methylcellulose-containing medium, then dispend into a regular 96 well plate and cultured at 37° C. and 5% $CO_2$ for the formation of aggregates (regular 96 well plate method).

5. Cells can be alternatively re-suspended in a Methylcellulose-containing medium, then dispended in droplets onto a Petri dish, then flip over the Petri dish to make upside down hanging droplets, and cultured at 37° C. and 5% $CO_2$ for the formation of aggregates (droplets method).
6. The cell aggregates may be made with pure dermal papilla cells, or a mixture of cell populations, including keratinocytes and/or melanocytes.
7. Upon cell aggregate formation, aggregates may be cultured in droplet, with proper culture medium, medium may be changed every other day, at 37° C. and 5% $CO_2$ for the development of proto-hairs.
8. Alternatively, aggregates may be placed into an eppendorf tube, non-adhesive 96 well plate, methylcellulose coated 96 well plate, matrix-gel material, any bio-compatible polymers and cultured in proper medium, medium may be changed every other day, at 37° C. and 5% $CO_2$ for the development of proto-hairs.
9. Cell aggregates may be cultured in a proper medium to allow hair development, the proper culture medium can be Chang, Epilife, Melanocyte-specific medium or mixture of above. Any growth factor(s), such as FGF, TGF-alpha, PDGF, any molecule(s), such as Wnt, GSK-3 inhibitors, shh or agonist, Noggin or BMP inhibitors, antibodies, iRNA, any chemical compound(s), such as Manoxdil, any cell-conditioned-medium, such as keratinocyte-conditioned medium, wnt-3a conditioned medium, may be added into the medium to promote proto-hair development. Alternatively,
1. Keratinocytes can be cultured on the surface of a layer of collagen gel to generate a keratinocyte sheet
2. The dermal papilla cells or dermal papilla cell aggregates are introduced to contact the keratinocyte sheet
3. Culture in a suitable medium to allow hairs to develop.
4. The proper culture medium can be Chang, Epilife, Melanocyte-specific medium or mixture of above. Any growth factor(s), such as FGF, TGF-alpha, PDGF, any molecule(s), such as Wnt, GSK-3 inhibitors, shh or agonist, Noggin or BMP inhibitors, antibodies, iRNA, any chemical compound(s), such as Manoxdil, any cell-conditioned-medium, such as keratinocyte-conditioned medium, wnt-3a conditioned medium, may be added into the medium to promote proto-hair development.

Example #1

Figure 2:
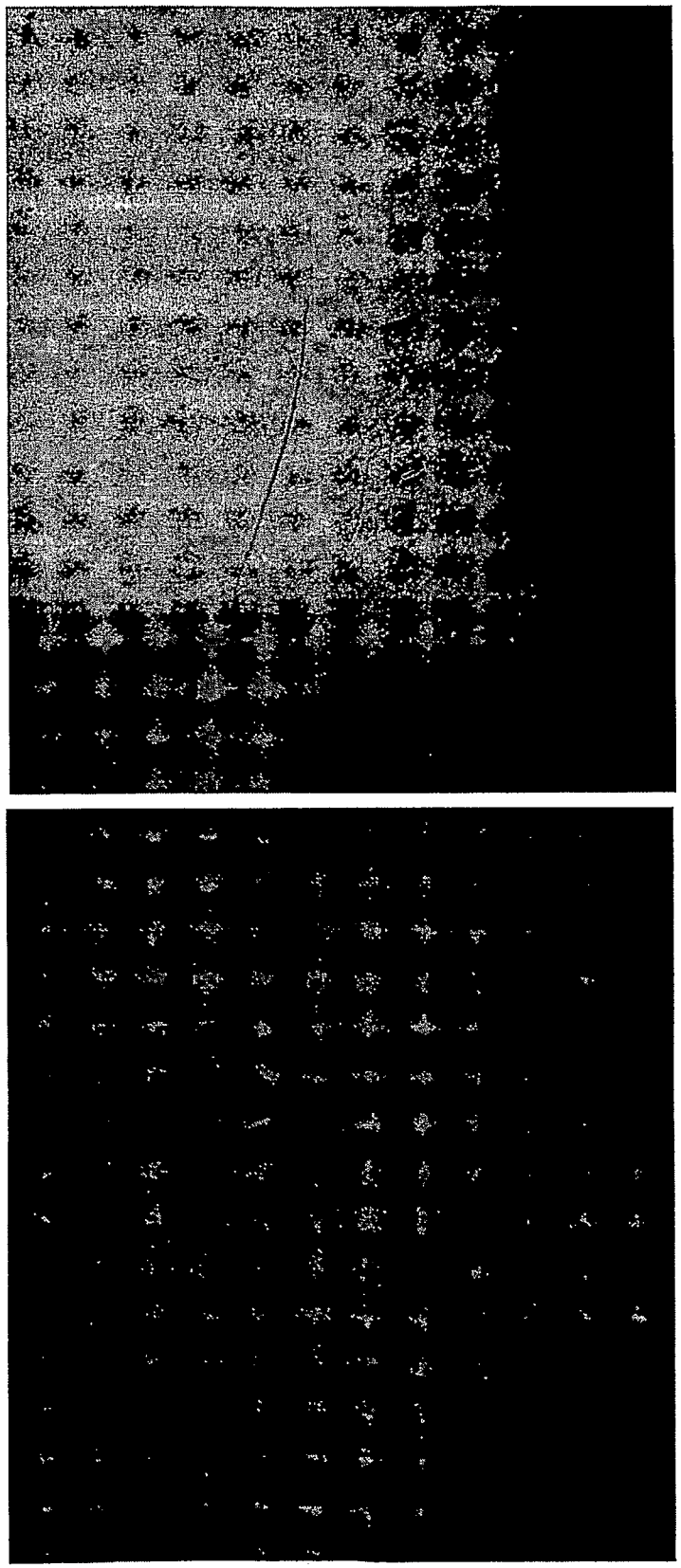

Dermal papilla cells and keratinocytes from embryonic skin were cultured in vitro in embryonic tissue matrix. Under these conditions, immature hair follicle structures (proto-hairs) formed within 6 days (see FIGS. 1A and 1B). The proto-hairs could be separated from the matrix and transplanted into the skin of an athymic mouse, and a mature hair could grow (see FIGS. 2A and 2B).

Example #2

Figure 3:
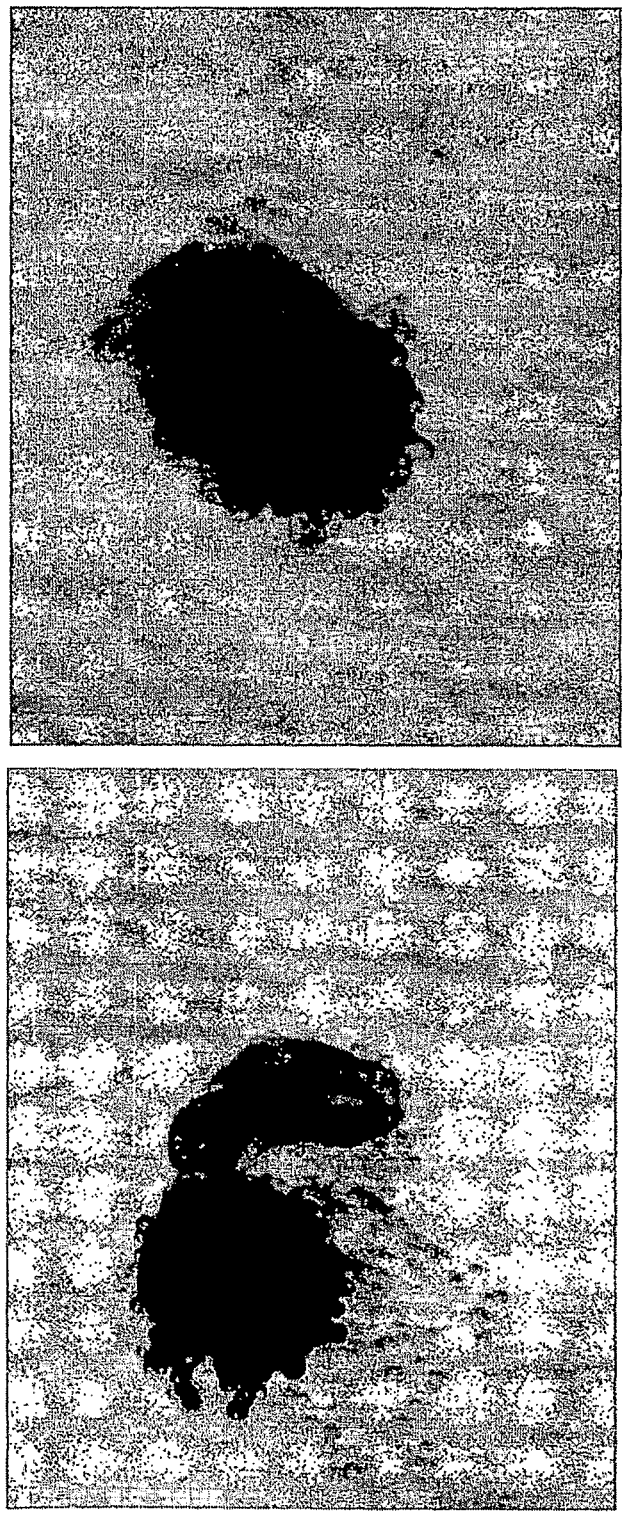
FIGS. 3A and 3B show hair development from aggregates prepared from dermal papilla cells and keratinocytes.
Figure 4:
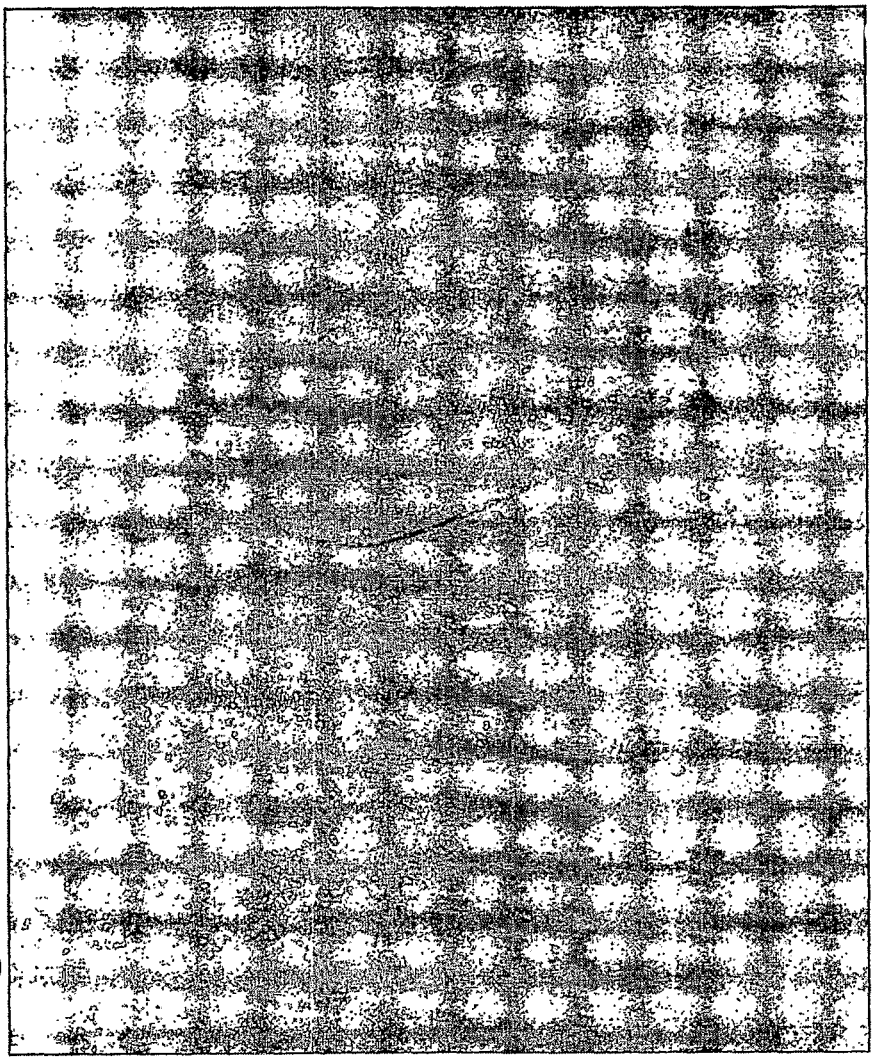
FIG. 4 shows the formation of a mature hair after transplantation of proto-hairs formed in vitro from a cell aggregate.

Dermal papilla cells and keratinocytes were combined into an aggregate using the hanging droplet method. The aggregates were incubated in culture medium and proto-hair structures formed (see FIGS. 3A and 3B). Individual proto-hairs were transplanted to the skin of an athymic mouse and the proto-hairs developed into mature hairs (see FIG. 4).

Example #3

Dermal papilla cells and keratinocytes were isolated from embryonic skin and combined onto a transwell membrane and cultured for 7 days. Immature hair follicle structures (proto-hairs) formed, some of which contained hair fibers visible in histological sections. (see FIGS. 5A and 5B)

Example #4

Cultured dermal papilla cells were layered onto a collagen matrix and then overlaid with a sheet of epidermal keratinocytes. Immature hair follicle structures formed. (See FIGS. 6A and 6B).

Example #5

Dermal papilla cells and keratinocytes from embryonic skin were cultured in vitro in embryonic tissue matrix. Cultures were treated with an antibody that inhibited hair development. The number of proto-hairs depended upon the concentration of the antibody (see FIGS. 7A, 7B, and 7C).

Example #6

Dermal papilla cells and keratinocytes from embryonic skin were cultured in vitro in embryonic tissue matrix. Cultures were treated with a growth factor that promoted hair development. The number of proto-hairs depended on the concentration of the growth factor (see FIGS. 8A, 8B, and 8C).

Example #7

Dermal papilla cells and keratinocytes from embryonic skin were cultured in vitro in embryonic tissue matrix. Cultures were treated with a reagent that increased the number of proto-hairs that formed (see FIGS. 9A and 9B).

What is claimed is:

1. A method for in vitro production of a precursor of a mature hair follicle or proto-hair comprising co-culturing mammalian dermal papilla cells, keratinocytes, and optionally melanocytes, wherein said co-culture produces a multicellular precursor of a mature hair follicle or proto-hair from a cultured cell aggregate, wherein the multicellular precursor of a mature hair follicle or proto-hair is at a stage of development between the dermal papilla cell stage and the fully formed follicle stage.

2. The method of claim 1, wherein the dermal papilla cells, keratinocytes, and melanocytes are of adult origin.

3. The method of claim 1, wherein the dermal papilla cells, keratinocytes, and melanocytes are of embryonic origin.

4. The method of claim 1, wherein the dermal papilla cells, keratinocytes, and melanocytes are of primary origin.

5. The method of claim 1, wherein the dermal papilla cells, keratinocytes, and melanocytes are obtained from separate dermal papilla cell, keratinocyte, and melanocyte cultures, respectively.

6. The method of claim 1, wherein the dermal papilla cells, keratinocytes, and melanocytes are of human origin.

7. The method of claim 1, wherein the dermal papilla cells, keratinocytes, and melanocytes are of autologous or allogeneic origin.

8. The method of claim 1, wherein the dermal papilla cells, keratinocytes, or melanocytes originate from the tissue of the head, body or foreskin.

9. The method of claim 1, wherein the dermal papilla cells, keratinocytes, and melanocytes originate from embryonic stem cells, bone marrow stem cells, umbilical cord stem cells, or any other committed and semi-committed hair progenitor cells.

10. The method of claim 1, wherein the cells are cultured on a matrix.

11. The method of claim 10, wherein the matrix is a bare dish, a coated dish, a bare trans-well membrane, a coated trans-well membrane, a biodegradable matrix gel or a non-biodegradable matrix gel.

12. The method of claim 1, wherein the dermal papilla cells, keratinocytes, and melanocytes are cultured in a medium that supports hair or precursor of a mature hair follicle growth.

13. The method of claim 12, wherein the medium comprises Chang medium, keratinocyte-conditioned medium, melanocyte-conditioned medium, or a mixture thereof.

14. The method of claim 1, comprising
 a) contacting a cultured dermal papilla population, a cultured keratinocyte cell population, and optionally a cultured melanocyte cell population;
 b) centrifuging the cell populations so that they sediment out;
 c) transferring the sedimented cell populations onto a trans-well membrane or other matrix; and
 d) culturing the cells to allow precursor to a mature hair follicle or proto-hair production.

15. The method of claim 1, comprising
 a) forming a cell aggregate by:
  i. mixing cultured dermal papilla cells, culturing keratinocytes, and optionally melanocytes, or
  ii. forming cell aggregates of pure, cultured dermal papilla, and collecting the cell aggregates and mixing the cell aggregates with cultured hair keratinocytes and optionally with melanocytes;
 b) transferring the cell aggregate onto a trans-well membrane or other matrix; and
 c) culturing the cells of the cell aggregate to allow precursor to a mature hair follicle or proto-hair production.

16. The method of claim 1, comprising
 a) providing a keratinocyte sheet
 b) contacting a dermal papilla cell or a dermal papilla cell aggregate with the keratinocyte sheet and optionally with melanocytes; and
 c) culturing the cells to allow precursor to a mature hair follicle or proto-hair production.

17. The method of claim 1, comprising isolating the precursor of a mature hair follicle or proto-hair.

* * * * *